United States Patent [19]

Layton

[11] 4,131,016
[45] Dec. 26, 1978

[54] PEAK FLOW MEASURING DEVICE

[75] Inventor: Terry N. Layton, Wheeling, Ill.

[73] Assignee: The Kendall Company, Boston, Mass.

[21] Appl. No.: 849,747

[22] Filed: Nov. 9, 1977

[51] Int. Cl.² .............................................. G01F 1/20
[52] U.S. Cl. ..................................... 73/215; 128/2 F;
128/295
[58] Field of Search ................. 73/194 R, 215, 421 R;
116/117 R; 128/2 F, 295

[56] References Cited
U.S. PATENT DOCUMENTS

| 2,648,981 | 8/1953 | Drake | 73/215 |
| 3,859,671 | 1/1975 | Tomasello | 128/2 F |
| 3,859,854 | 1/1975 | Dye | 73/215 |
| 3,871,231 | 3/1975 | Ciarico | 73/215 |

*Primary Examiner*—Herbert Goldstein
*Attorney, Agent, or Firm*—Powell L. Sprunger

[57] ABSTRACT

A device for measuring the peak flow rate of a urine discharge comprising, a hollow receptacle having a chamber, an inlet port for passage of the discharge into the chamber, and an outlet port for passage of the discharge from the chamber at a predetermined flow rate. The device has a collection container having a closed bottom, a cavity, and an opening adjacent an upper end of the container. The receptacle has an aperture in a lower wall of the receptacle to removably receive the container with the container opening located a predetermined height above the receptacle lower wall in the chamber, such that the discharge passes from the chamber into the container cavity at a predetermined height of the liquid in the receptacle chamber.

8 Claims, 4 Drawing Figures

U.S. Patent        Dec. 26, 1978        4,131,016
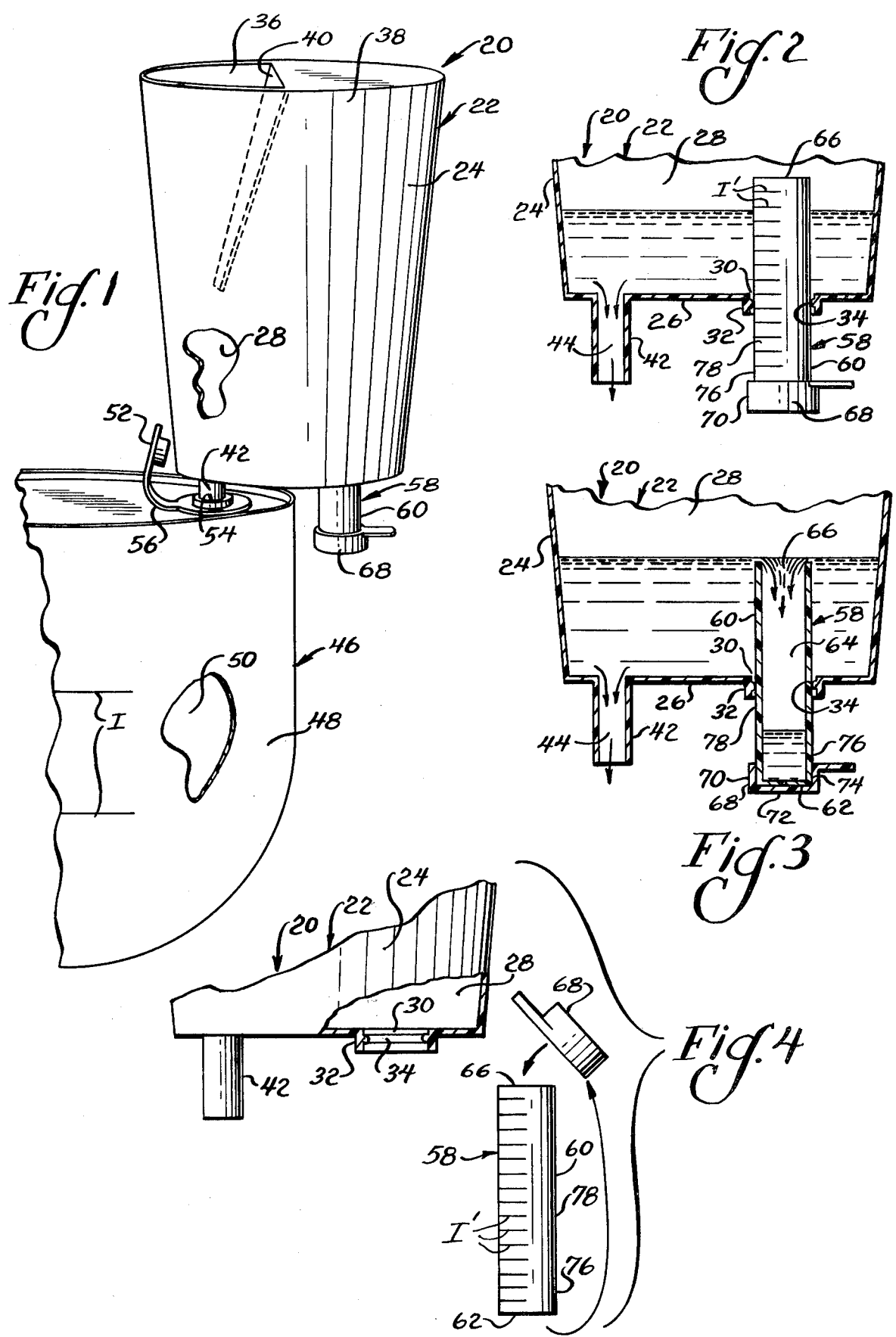

PEAK FLOW MEASURING DEVICE

BACKGROUND OF THE INVENTION

The present invention relates to a device for measuring a discharge of urine.

In the past, it has been found desirable to obtain various data pertaining to a liquid discharge. In particular, it was discovered that many urological problems could be readily diagnosed by analyzing information obtained during the natural voiding of urine by patients. Presently, various types of devices are utilized to obtain data on the urine stream, such as total volume, average flow rate, force, velocity, and configuration of the stream.

Most of these devices have suffered from less than total reliability because they have required the presence of one or more observers while the patient is voiding. It is obvious that administration of such devices in this manner creates sufficient psychological difficulties for many of the patients to effect voiding. Consequently, if the patients void at all, the potentially erroneous data obtained may result in a false diagnosis and a loss of confidence in the device by the physician. A further complication arises from the fact that many of these devices are rather bulky, and somewhat difficult to use.

SUMMARY OF THE INVENTION

A principal feature of the present invention is the provision of a device of simplified construction for measuring a discharge of urine, and which may be self-administered by a patient.

The device of the present invention comprises, a hollow receptacle having sidewalls at least partially defining a chamber, a lower wall having an aperture, an inlet port adjacent an upper end of the receptacle and communicating with the chamber to receive the discharge for passage into the chamber, and an outlet port adjacent a lower end of the receptacle and communicating with the chamber for passage of the discharge at a predetermined rate out of the chamber. The device has a collection container having a closed bottom, an elongated generally tubular section defining a collection cavity in the container, and an opening adjacent an upper end of the container communicating with the cavity. The container is removably received in the receptacle aperture with the container opening spaced a predetermined distance above the lower receptacle wall in the receptacle chamber, and with the receptacle sealingly engaging against an outer surface of the container.

A feature of the present invention is that the urine discharge collects in the receptacle chamber, and passes from the chamber into the container cavity if and only if the peak flow rate of the discharge is greater than a predetermined value.

Another feature of the invention is that the device thus provides a discrete indication whether the peak flow rate of the urine discharge is above or below a predetermined value as determined by passage or nonpassage respectively of the discharge into the container cavity.

A further feature of the invention is that the predetermined peak flow rate value is established by the height of the container opening in the chamber, and the discrete peak flow rate value may be preselected by adjusting the height of the container opening in the receptacle chamber.

Thus, a feature of the present invention is that the device may be utilized to assess the patient's ability to void by determining whether the peak flow rate of the discharge is above or below the predetermined value.

Another feature of the invention is that the device may be self-administered by the patient.

Still another feature of the invention is that the container may be removed from the receptacle after voiding to provide a convenient specimen of urine for analysis.

Further features will become more fully apparent in the following description of the embodiments of this invention and from the appended claims.

DESCRIPTION OF THE DRAWINGS

In the drawings:

FIG. 1 is a fragmentary perspective view, partly broken away, of a urine measuring device of the present invention;

FIG. 2 is a fragmentary view, taken partly in section, illustrating a lower part of a receptacle in the device of FIG. 1 and a container to receive accumulated urine above a predetermined peak flow rate of a urine discharge;

FIG. 3 is a fragmentary sectional view of the device of FIG. 2 illustrating passage of accumulated urine into the container responsive to a peak flow rate above the predetermined amount; and FIG. 4 is a fragmentary elevational view, taken partly in section, of the device illustrating use of the container for handling a urine specimen.

DESCRIPTION OF THE PREFERRED EMBODIMENTS

Referring now to FIGS. 1-3, there is shown a device generally designated 20 for measuring the peak flow rate of a urine discharge. The device 20 has a hollow receptacle generally designated 22 having sidewalls 24 and a lower wall 26 defining a chamber 28 in the receptacle 22. The receptacle 22 has an aperture 30 defined by a flange 32 depending from the receptacle lower wall 26, with the flange 32 having a sealing ring 34 extending peripherally around the aperture 30. The receptacle 22 also has an inlet port 36 adjacent an upper end 38 of the receptacle, and a diverting plate 40 below the inlet port 36 to direct the incoming discharge into the chamber 28 away from the receptacle aperture 30. The receptacle 22 has a tubular section 42 depending from the receptacle lower wall 26 and defining an outlet port 44 communicating with the chamber 28 and controlling passage of liquid from the receptacle chamber 28 at a predetermined flow rate.

With reference to FIG. 1, the device 20 may also have a collection bag generally designated 46 having flexible sidewalls 48 defining a cavity 50 in the bag. The bag 46 has an upper opening 54 to releasably receive the receptacle tubular section 42 such that the receptacle outlet port communicates with the bag cavity 50 for passage of the urine at a predetermined flow rate from the receptacle chamber 28 into the bag cavity 50. If desired, the bag 46 may have a cap 52 to close the bag opening 54 when the bag is removed from the receptacle, with the cap 52 being connected by a strap 56 to the bag 46. If desired, the bag sidewalls 48 may be made from a transparent plastic material, and may have indicia I on an outer surface of the sidewalls 48 to provide an indication of the volume of urine collected in the bag cavity 50.

With reference to FIGS. 1-3, the device 20 also has a collection container or vial generally designated 58 having a transparent cylindrical sidewall 60 and a bottom wall 62 defining a cavity 64 in the container, with the container sidewall 60 defining an opening 66 at the top or upper part of the vial. As shown, the container 58 may have a cap 68 having an annular sidewall 70 and top wall 72 defining a recess 74 in the cap 68 which is dimensioned to snugly and releasably receive a lower part 76 of the vial 58. With reference to FIG. 2, the vial 58 may have calibrated indicia I' on an outer surface 78 of the sidewall 60 for use in positioning the vial 58 in the receptacle 22, and for use in connection with the volume of urine which may eventually be collected in the vial cavity 64.

As shown in FIGS. 1-3, the vial 58 is slidably received in the receptacle aperture 30 with the receptacle sealing ring 34 sealingly engaging against the outer surface 78 of the vial to prevent passage of liquid through the aperture 30 between the receptacle and the vial. The longitudinal position of the vial 58 in the receptacle aperture 30 may be adjusted to modify the height of the vial opening 66 above the receptacle lower wall 26 and the lower part of the chamber 28.

In use of the device, the cap 52 of the collection bag 46 is removed from the opening 54, and the bag 46 is attached to the receptacle tubular extension 42. In addition, the collection vial 58 is placed in the receptacle aperture 30 with the vial opening 66 located at a desired height in the chamber 28 as determined by the indicia I' to provide a preselected peak flow rate value of the urine discharge, as will be further discussed below.

The inlet port 36 of the receptacle 22 is then positioned by a patient in privacy to receive the discharge of urine. With reference to FIG. 2, as the liquid discharge passes through the port 36 into the receptacle chamber 28 it begins to collect in the lower part of the receptacle chamber 28 and pass through the outlet port 44 into the collection bag 46. As previously indicated, the tubular section 42 defining the outlet port 44 establishes a predetermined flow rate of the liquid discharge from the receptacle chamber 28, and if the flow rate of urine through the outlet port 44 is greater than the flow rate of the urine discharge into the receptacle, the urine will pass into the collection bag 46 without accumulating significantly in the receptacle chamber. Thus, under such a condition of relatively low discharge flow rate, the urine which accumulates in the receptacle chamber 28 will not attain the height of the vial opening 66 assuming that it has been positioned a sufficient height above the receptacle lower wall 26.

However, in the normal case, the flow rate of the urine discharge passing into the receptacle chamber 28 will be greater than the predetermined flow rate of the accumulated discharge through the outlet port 44, such that the height of collected liquid in the receptacle chamber 28 will rise as the discharge passes into the receptacle. In the event that the peak or maximum flow rate is less than the predetermined value, the height of accumulated liquid in the receptacle chamber 28 will not reach the level of the vial opening 66 which has been set at a predetermined distance above the container lower wall 26. In this case, the liquid will accumulate to a maximum height in the receptacle chamber 28 below the vial opening 66, and all of the liquid will eventually pass through the outlet port 44 of the receptacle 22 as voiding ceases and the height of collected liquid in the chamber 28 abates.

In the event that the peak flow rate of the urine discharge is greater than the predetermined amount, the height of liquid in the receptacle chamber 28 rises above the level of the vial opening 66, such that the liquid begins to pass through the vial opening 66 into the vial cavity 64, as illustrated in connection with FIG. 3. Thus, passage of urine from the chamber 28 into the vial cavity 64 during voiding provides an indication that the peak flow rate of the urine discharge is greater than a predetermined value as determined by the height adjustment of the vial opening 66 in the receptacle 22. Accordingly, passage or non-passage of the urine discharge into the vial provides a discrete indication whether the peak flow rate of the urine discharge is respectively greater or less than a predetermined amount. The device 20 may thus be utilized to diagnose patients for possible further treatment by determining whether the peak flow rate of the patient's urine discharge is greater or less than a desired value.

After voiding by the patient has ceased, the collected urine in the receptacle chamber 28 drains through the outlet port 44 into the collection bag 46. If desired, the approximate total volume of collected urine in the bag 46 may be determined by the indicia I on the bag. Further, assuming that the peak flow rate of the patient's discharge was greater than the predetermined amount such that urine passed into the collection vial, the vial 58 may be removed from the receptacle 22, as illustrated in connection with FIG. 4, and a specimen of urine is thus located in the vial cavity for convenient access. The cap 68 may be removed from the lower part of the vial and placed over the upper part of the vial to cover the vial opening 66 and retain the specimen for later analysis, if desired. Alternatively, if the peak flow rate of the discharge was less than the predetermined value such that the urine did not pass into the vial 58, the collection bag 46 may be removed from the receptacle 22, and a specimen may be obtained through the bag opening 54.

Thus, in accordance with the present invention, the device 20 provides a discrete indication whether the peak flow rate of a patient's discharge is greater or less than a predetermined value as determined through suitable adjustment of the vial in the receptacle. Further, the device provides a convenient sample of the urine for subsequent analysis, if desired.

The foregoing detailed description is given for clearness of understanding only, and no unnecessary limitations should be understood therefrom, as modifications will be obvious to those skilled in the art.

I claim:

1. A device for measuring a urine discharge, comprising:
   a hollow receptacle having sidewalls at least partially defining a chamber, a lower wall having an aperture communicating between the chamber and atmosphere, an inlet port adjacent an upper end of the receptacle and communicating with the chamber to receive the discharge for passage into the chamber, and an outlet port adjacent a lower end of the receptacle and communicating with the chamber for passage of the discharge at a predetermined rate out of the chamber;
   a collection container having a closed bottom, an elongated generally tubular section defining a collection cavity in the container, and an opening adjacent an upper end of the container communicating with said cavity, said container being removably received in the receptacle aperture with the container opening spaced a predetermined distance above the lower receptacle wall in said chamber, and with the receptacle sealingly engaging against a surface of the container in the region of said aperture, such that the discharge passes from the receptacle chamber through the container opening into said cavity at a predetermined height of the liquid in said chamber to provide a discrete indication of the discharge peak flow rate and a specimen of the discharge in said cavity for analysis upon removal of the container from the receptacle.

2. The device of claim 1 including a cap for releasable attachment to an upper part of said container and closure of said opening.

3. The device of claim 1 wherein said cap is releasably attached to the bottom of said container in a storage position when the container is received in the receptacle aperture.

4. The device of claim 1 including a collection bag communicating with said receptacle outlet port to receive the discharge passing from the outlet port.

5. The device of claim 1 wherein said receptacle includes a sealing ring sealingly engaging the outer surface of the container peripherally around said aperture.

6. The device of claim 1 wherein said container is adjustably positioned in said receptacle aperture to modify the height of the container opening above the receptacle lower wall.

7. The device of claim 1 wherein the receptacle includes means for directing the incoming discharge away from the container opening.

8. The device of claim 1 wherein the container comprises a vial having a cylindrical sidewall defining the cavity, a bottom wall closing a lower end of the cavity, and the opening defined by the top of the sidewall.

* * * * *